United States Patent
Li et al.

(10) Patent No.: US 10,004,272 B2
(45) Date of Patent: Jun. 26, 2018

(54) ATOMIZER AND ELECTRONIC CIGARETTE HAVING SAME

(71) Applicant: Shenzhen First Union Technology Co., Ltd., Shenzhen, Guangdong Province (CN)

(72) Inventors: Yonghai Li, Shenzhen (CN); Zhongli Xu, Shenzhen (CN); Yindeng Deng, Shenzhen (CN); Yunping Zhong, Shenzhen (CN)

(73) Assignee: SHENZHEN FIRST UNION TECHNOLOGY CO., LTD., Shenzhen, Guangdong Province (CN)

( * ) Notice: Subject to any disclaimer, the term of this patent is extended or adjusted under 35 U.S.C. 154(b) by 0 days. days.

(21) Appl. No.: 15/408,400

(22) Filed: Jan. 17, 2017

(65) Prior Publication Data
US 2017/0119061 A1 May 4, 2017

(30) Foreign Application Priority Data
Jan. 29, 2016 (CN) .................... 2016 2 0089236 U

(51) Int. Cl.
A24F 47/00 (2006.01)
(52) U.S. Cl.
CPC .................. *A24F 47/008* (2013.01)

(58) Field of Classification Search
CPC ........ A24F 47/008; A24F 7/02; A24F 47/004; A24F 47/002; F16J 15/022; H05B 6/36; H05B 6/362; H05B 6/108; F16K 15/025; F22B 1/284
USPC ............. 131/329, 194, 271, 273; 128/202.21
See application file for complete search history.

(56) References Cited

U.S. PATENT DOCUMENTS

| 8,156,944 B2 * | 4/2012 | Han .................... A24F 47/008 128/202.21 |
| 2007/0267031 A1 * | 11/2007 | Hon .................... A24F 47/008 131/273 |
| 2015/0250231 A1 * | 9/2015 | Hon .................... A24F 47/008 131/329 |

* cited by examiner

*Primary Examiner* — Edwin A. Leon
(74) *Attorney, Agent, or Firm* — Cheng-Ju Chiang

(57) ABSTRACT

An exemplary atomizer includes a housing, an atomizing core arranged in the housing, a mouthpiece at an end of the housing. The housing defines a liquid chamber configured for storing tobacco liquid. The atomizing core is configured for atomizing tobacco liquid to form aerosol. The atomizer further includes an air pipe arranged between the atomizing core and the mouthpiece. The air pipe is configured for guiding the aerosol to pass through. The atomizer further includes a porous body arranged in the air pipe adjacent to the mouthpiece, and the porous body is configured for absorbing a liquid drop, into which the aerosol condenses.

20 Claims, 4 Drawing Sheets

ATOMIZER AND ELECTRONIC CIGARETTE HAVING SAME

TECHNICAL FIELD

The present invention relates to electronic cigarettes, and particularly to an atomizer and an electronic cigarette using same.

BACKGROUND ART

A typical electronic cigarette includes an atomizer and a power supply, and the atomizer includes an atomizing core, an air passage, and a mouthpiece. The atomizing core is configured for heating tobacco liquid to form aerosol. The aerosol passes through the air passage and reaches the mouthpiece, and is then inhaled by a user of the electronic cigarette. However, the aerosol may condense into liquid drops in air passage, and then the liquid drops may be sucked by the user, thus rendering user experience unsatisfactory.

What are needed, therefore, are an atomizer and an electronic cigarette using same, which can overcome the above shortcomings.

SUMMARY

An exemplary atomizer includes a housing, an atomizing core arranged in the housing, a mouthpiece at an end of the housing. The housing defines a liquid chamber configured for storing tobacco liquid. The atomizing core is configured for atomizing tobacco liquid to form aerosol. The atomizer further includes an air pipe arranged between the atomizing core and the mouthpiece. The air pipe is configured for guiding the aerosol to pass through. The atomizer further includes a porous body arranged in the air pipe adjacent to the mouthpiece, and the porous body is configured for absorbing a liquid drop, into which the aerosol condenses.

BRIEF DESCRIPTION OF THE DRAWINGS

Many aspects of the present disclosure can be better understood with reference to the following drawings. The components in the drawings are not necessarily drawn to scale, the emphasis instead being placed upon clearly illustrating the principles of the present disclosure. Moreover, in the drawings, like reference numerals designate corresponding parts throughout the several views.

DETAILED DESCRIPTION

Figure 1:
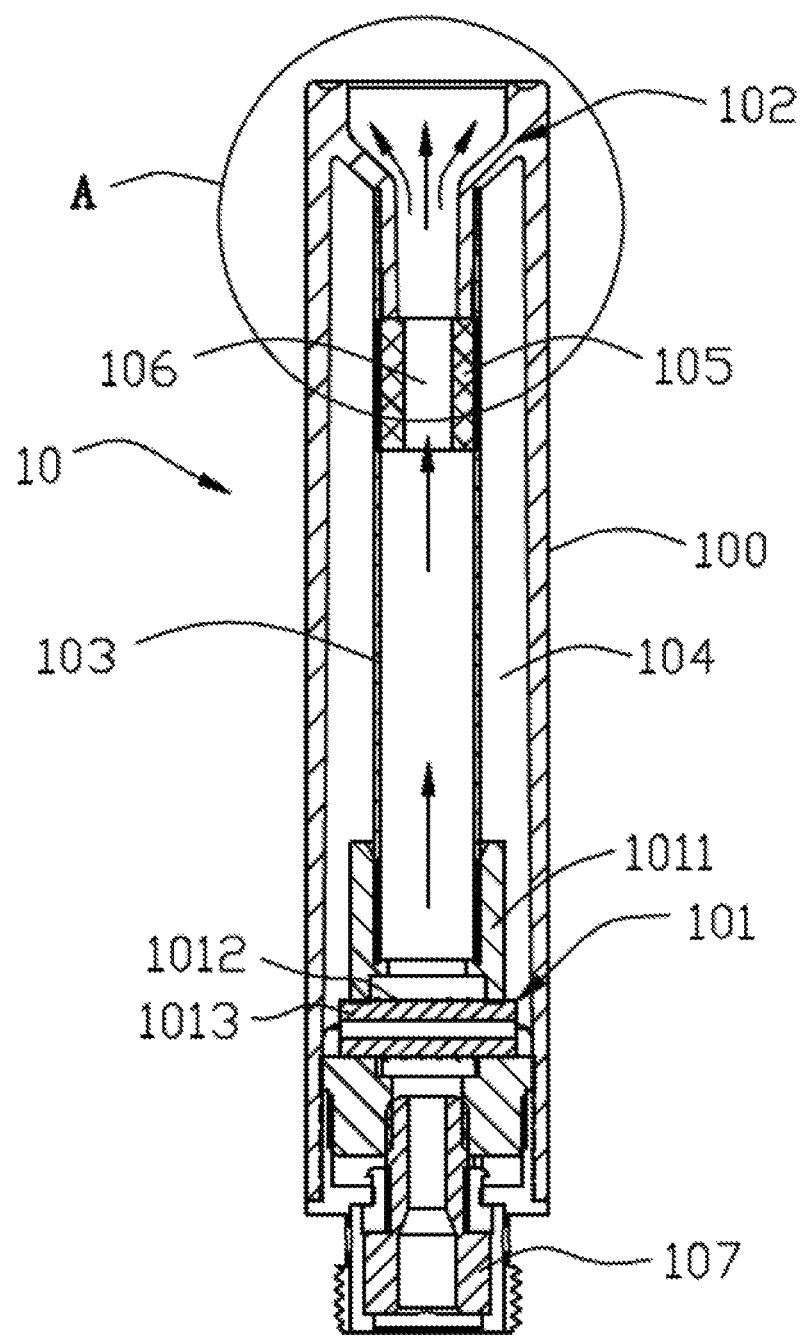
FIG. 1 is a cross-sectional view of an atomizer according to a first embodiment.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts have been exaggerated to better illustrate details and features of the present disclosure.

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Several definitions that apply throughout this disclosure will now be presented.

The term "outside" refers to a region that is beyond the outermost confines of a physical object. The term "inside" indicates that at least a portion of a region is partially contained within a boundary formed by the object. The term "substantially" is defined to be essentially conforming to the particular dimension, shape or other word that substantially modifies, such that the component need not be exact. For example, substantially cylindrical means that the object resembles a cylinder, but can have one or more deviations from a true cylinder. The term "comprising," when utilized, means "including, but not necessarily limited to"; it specifically indicates open-ended inclusion or membership in the so-described combination, group, series and the like.

Referring to FIG. 1, an atomizer 10 for an electronic cigarette according to an embodiment is shown. The atomizer 10 includes a housing 100, an atomizing core 101 in the housing 100, and an air pipe 103. A mouthpiece 102 is provided at an end of the housing 100, and an electrode part 107 is provided at an opposite end of the housing 100. The electrode part 107 is electrically connected with the atomizing core 101, and configured (i.e., structured and arranged) for connecting with a power supply. The housing 100 defines a liquid chamber 104 configured for storing tobacco liquid. The atomizing core 101 is configured for atomizing the tobacco liquid to form aerosol. The air pipe 103 is arranged between the atomizing core 101 and the mouthpiece 102, and configured for guiding the aerosol to pass through. The aerosol passes through the air pipe 103, and is then sucked from the mouthpiece 102. A porous body 105 is provided in the air pipe 103 adjacent to the mouthpiece 102, and is configured for absorbing liquid drops, into which the aerosol condenses. The porous body 105 is a micro porous structure, and has a strong adsorptivity. The porous body 105 is engaged in an inner wall of the air pipe 105 by interference fit. The aerosol generated by the atomizing core 101 flows to the mouthpiece 102 along the air pipe 105, and is gradually cooled to condense into liquid drops. The liquid drops are absorbed by the porous body 105, and accordingly, are prevented from sucking by a user of the electronic cigarette.

In detail, the porous body 105 is air permeable so that air and aerosol can pass through; the porous body 105 has a porous structure, so that the porous body 105 has an adsorptivity or is hydrophilic. Quite usefully, the porous body 105 is made of porous polyethylene, porous cellulose acetate fiber, or porous fiber cotton. To make air flow through the porous body more smoothly, the porous body 105 defines a central through hole 106 along an axial direction.

Figure 2:
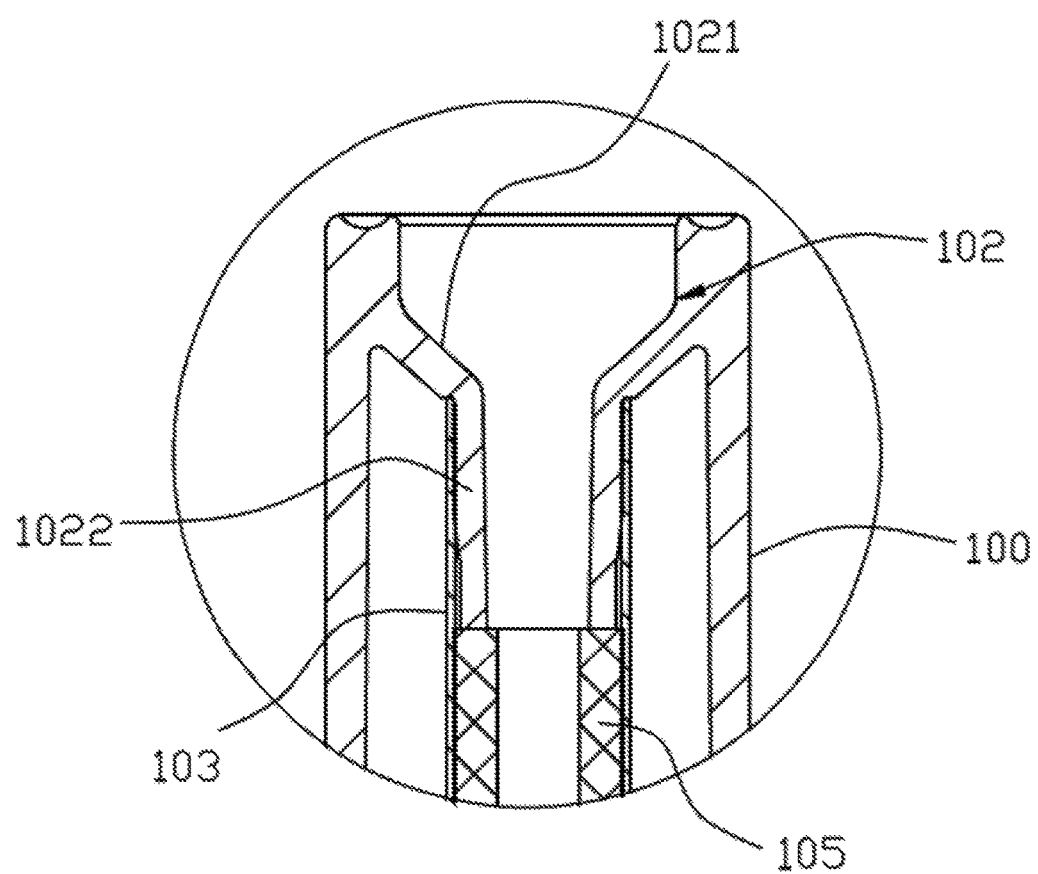
FIG. 2 is an enlarged view of area A in FIG. 1.

Referring to FIG. 2, quite usefully, the mouthpiece 102 includes a funnel part 1021 with a large opening and a tubular connecting part 1022 extending from a bottom part of the funnel part 1021. One end of the air pipe 103 sleeves the connecting part 1022, and the porous body 105 is arranged below the connecting part 1022. It is to be understood that the porous body 105 may be arranged in the connecting part 1022. An internal diameter of the funnel part 1021 is larger than that of the air pipe 103, a speed of airflow in the funnel part 1021 is slowed, and accordingly, a risk of sucking liquid drops is further decreased. Simultaneously, liquid drops condensed on an inner wall of the mouthpiece 102, can flow back and are absorbed by the porous body 105. In the present embodiment, the funnel part 1021, the connecting part 1022 and the housing 11 are integrally formed, and made of plastic, thus simplifying a process of assembling.

Figure 3:
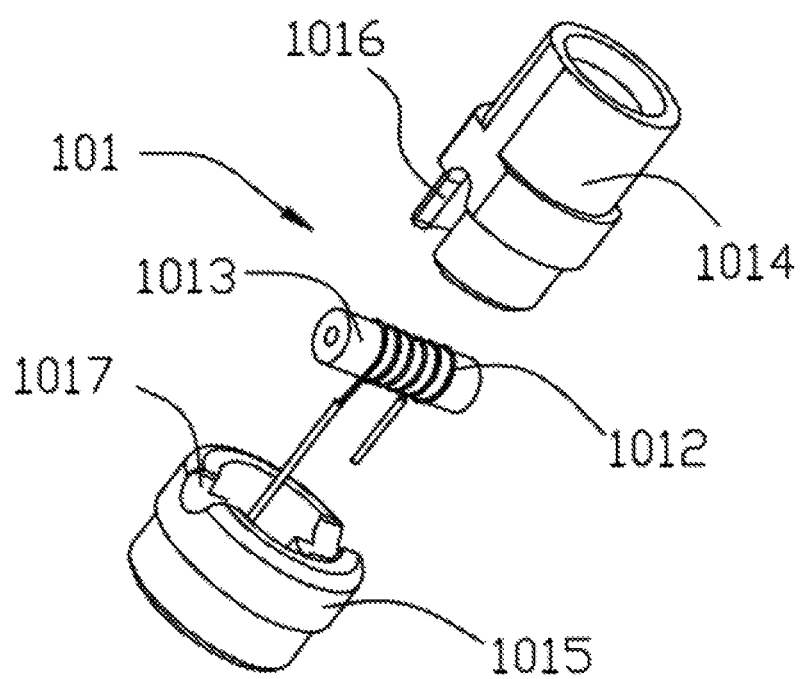
FIG. 3 is an exploded perspective view of an atomizing core of the atomizer of FIG. 1.

Referring to FIGS. 1 and 3, the atomizing core 101 includes a hollow fixing holder 1011, a liquid conducting element fixed in the fixing holder 1011, and a heating element for heating the tobacco liquid to form aerosol. An end of the air pipe 103 is connected with the fixing holder 1011, and the air pipe 103 communicates with internal space of the fixing holder 1011.

The fixing holder 1011 is made of silicone. The fixing holder 1011 is arranged at a bottom part inside the housing 100, and is hermetically coupled with an inner wall of the housing 100. Two opposite ends of the air pipe 103 are hermetically engaged with the connecting part 1022 and the fixing holder 1011. The housing 100, the mouthpiece 102, the air pipe 103, and the fixing holder 1011 cooperatively define the liquid chamber 104.

Quite usefully, the liquid conducting element is a micro porous ceramic rod 1013, and the heating element is a heating wire 1012 wound around the ceramic rod 1013. Two ends of the heating wire 1012 are connected with the electrode part 107. Two opposite ends of the ceramic rod 1013 extend through the fixing holder 1011, and contact with the tobacco liquid in the liquid chamber 104. The tobacco liquid permeates from two ends of the ceramic rod 1013 towards a middle part of the ceramic rod 1013, and is then heated by the heating wire 1012. The ceramic rod 1013 defines a centrally through hole along an axial direction, so that adequate tobacco liquid permeates into the ceramic rod 1013. It is to be noted that, in other embodiments, the heating element may be a heating piece, or a heating layer, and etc.

The fixing holder 1011 includes a top fixing holder 1014 and a bottom fixing holder 1015, both of which are made of silicone. The top fixing holder 1014 defines a first gap 1016 matching with the ceramic rod 1013, and the bottom fixing holder 1015 defines a second gap 1017 matching with the ceramic rod 1013. The top and the bottom fixing holders 1014, 1015 are coupled with each other in a manner that the first gap 1016 is aligned with the second gap 1017, with the ceramic rod 1013 clamped therebetween. Two opposite ends of the ceramic rod 1013 exposes out from the top and the bottom fixing holders 1014, 1015.

Figure 4:
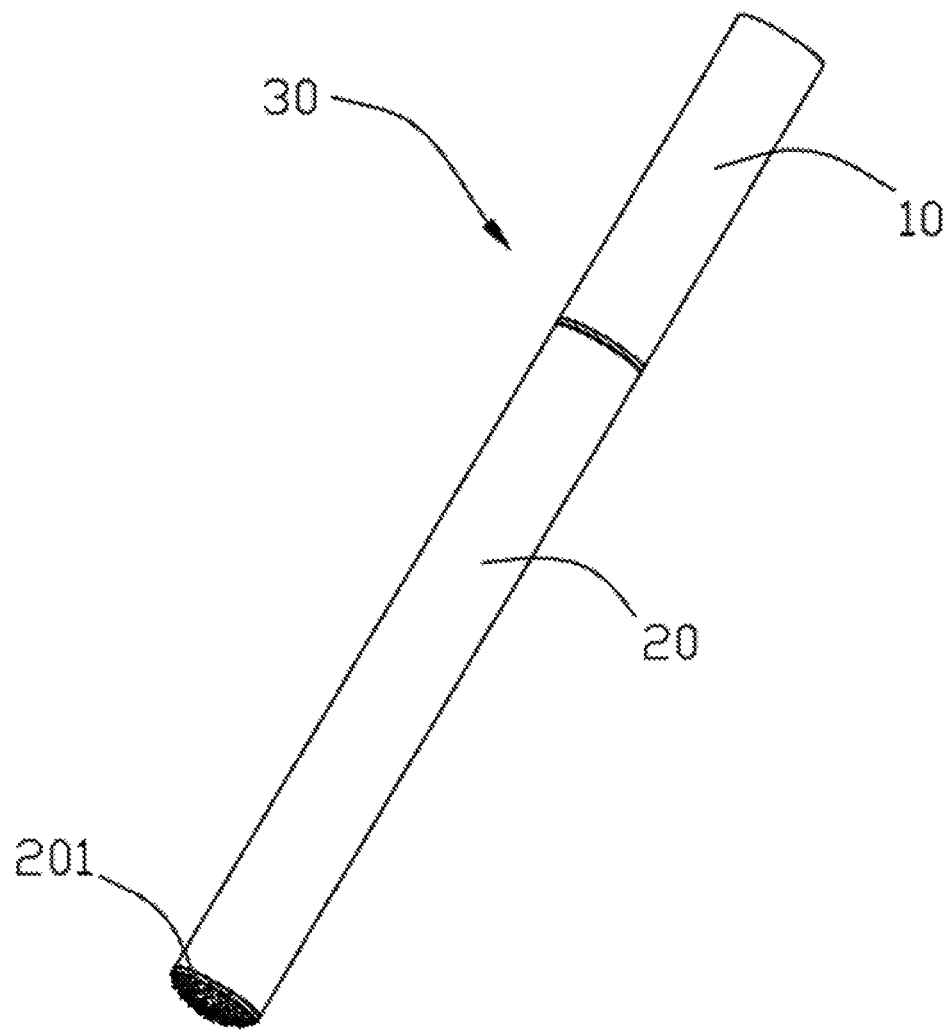
FIG. 4 is a perspective view of an electronic cigarette according to a second embodiment.

Referring to FIG. 4, an electronic cigarette 30 is shown. The electronic cigarette 30 includes the above-mentioned atomizer 10 and a power supply 20 detachably connected with the atomizer 10. The power supply 20 is configured for feeding the atomizer 10 power. The power supply 10 includes a light emitting diode (LED, not shown) inside, and a lampshade 201 at an end. When the electronic cigarette 30 works, the LED is turned on, thus stimulating burning of a traditional cigarette.

It is understood that the above-described embodiments are intended to illustrate rather than limit the disclosure. Variations may be made to the embodiments and methods without departing from the spirit of the disclosure. Accordingly, it is appropriate that the appended claims be construed broadly and in a manner consistent with the scope of the disclosure.

What is claimed is:

1. An atomizer for an electronic cigarette, comprising:
a housing defining a liquid chamber configured for storing tobacco liquid;
an atomizing core arranged in the housing, the atomizing core configured for atomizing tobacco liquid directly from the liquid chamber to form aerosol; and
a mouthpiece at an end of the housing;
wherein the atomizer further comprises an air pipe arranged between the atomizing core and the mouthpiece, and extending along an axis of the housing to isolate an inner space of the air pipe from the stored tobacco liquid of the liquid chamber, the air pipe is configured for guiding the aerosol generated from the atomizing core to pass through the liquid chamber, the atomizer further comprises a porous body arranged in the air pipe adjacent to the mouthpiece, and the porous body is configured for absorbing a liquid drop, into which the aerosol condenses.

2. The atomizer according to claim 1, wherein the porous body is made of material consisting of porous polyethylene, porous cellulose acetate fiber, and porous fiber cotton.

3. The atomizer according to claim 2, wherein the porous body defines a central through hole allowing air to pass through.

4. The atomizer according to claim 1, wherein the mouthpiece comprises a funnel part with a large opening and a connecting part extending from a bottom part of the funnel part, and an end of the air pipe sleeves the connecting part.

5. The atomizer according to claim 4, wherein the funnel part, the connecting part, and the housing are integrally formed.

6. The atomizer according to claim 1, wherein the atomizing core comprises a hollow fixing holder, a liquid conducting element fixed in the fixing holder, and a heating element for heating the tobacco liquid to form aerosol; an end of the air pipe is connected with the fixing holder, and the air pipe communicates with an internal space of the fixing holder.

7. The atomizer according to claim 6, wherein the housing, the mouthpiece, the air pipe, and the fixing holder cooperatively define the liquid chamber.

8. The atomizer according to claim 7, wherein the liquid conducting element comprises a micro porous rod, the heating element comprises a heating wire wound around the porous rod, and the ceramic rod extends through the fixing holder to contact with the tobacco liquid in the liquid chamber.

9. The atomizer according to claim 8, wherein the fixing holder comprises a top fixing holder and a bottom fixing holder, the top fixing holder defines a first gap matching with the ceramic rod, and the bottom fixing holder defines a second gap matching with the ceramic rod; the top and the bottom fixing holders are coupled with each other in a manner that the first gap is aligned with the second gap, with the ceramic rod clamped therebetween.

10. The atomizer according to claim 8, wherein the ceramic rod defines a central through hole along an axial direction thereof.

11. An electronic cigarette, comprising:
an atomizer according to claim 1; and
a power supply connected to the atomizer, the power supply being configured for supplying the atomizer power.

12. The electronic cigarette according to claim 11, wherein the porous body is made of material consisting of porous polyethylene, porous cellulose acetate fiber, and porous fiber cotton.

13. The electronic cigarette according to claim 12, wherein the porous body defines a central through hole allowing air to pass through.

14. The electronic cigarette according to claim 11, wherein the mouthpiece comprises a funnel part with a large opening and a connecting part extending from a bottom part of the funnel part, and an end of the air pipe sleeves the connecting part.

15. The electronic cigarette according to claim 14, wherein the funnel part, the connecting part, and the housing are integrally formed.

16. The electronic cigarette according to claim 11, wherein the atomizing core comprises a hollow fixing holder, a liquid conducting element fixed in the fixing holder, and a heating element for heating the tobacco liquid to form aerosol; an end of the air pipe is connected with the fixing holder, and the air pipe communicates with an internal space of the fixing holder.

17. The electronic cigarette according to claim 16, wherein the housing, the mouthpiece, the air pipe, and the fixing holder cooperatively define the liquid chamber.

18. The electronic cigarette according to claim 17, wherein the liquid conducting element comprises a micro porous rod, the heating element comprises a heating wire wound around the porous rod, and the ceramic rod extends through the fixing holder to contact with the tobacco liquid in the liquid chamber.

19. The electronic cigarette according to claim 18, wherein the fixing holder comprises a top fixing holder and a bottom fixing holder, the top fixing holder defines a first gap matching with the ceramic rod, and the bottom fixing holder defines a second gap matching with the ceramic rod; the top and the bottom fixing holders are coupled with each other in a manner that the first gap is aligned with the second gap, with the ceramic rod clamped therebetween.

20. An atomizer for an electronic cigarette, comprising:
a housing defining a liquid chamber configured for storing tobacco liquid;
an atomizing core arranged in the housing, the atomizing core configured for atomizing tobacco liquid to form aerosol; and
a mouthpiece at an end of the housing;
wherein the atomizer further comprises an air pipe arranged between the atomizing core and the mouthpiece, the air pipe is configured for guiding the aerosol to pass through; the atomizer further comprises a porous body arranged in the air pipe adjacent to the mouthpiece, and the porous body is configured for absorbing a liquid drop, into which the aerosol condenses; and
the atomizing core comprises a hollow fixing bolder, a liquid conducting element fixed in the fixing holder, and a heating element for heating the tobacco liquid to form aerosol; an end of the air pipe is connected with the fixing holder, and the air pipe communicates with an internal space of the fixing holder.

* * * * *